United States Patent [19]

Irikura et al.

[11] Patent Number: 4,791,225
[45] Date of Patent: Dec. 13, 1988

[54] HALOGENOBENZOIC ACID DERIVATIVES AND THEIR PREPARATION

[75] Inventors: Tsutomu Irikura, Tokyo; Seigo Suzue, Kuki; Satoshi Murayama, Tochigi; Keiji Hirai, Kuki; Takayoshi Ishizaki, Saitama, all of Japan

[73] Assignee: Kyorin Pharmaceutical Co., Ltd., Tokyo, Japan

[21] Appl. No.: 4,042

[22] Filed: Jan. 16, 1987

[30] Foreign Application Priority Data

Jan. 20, 1986 [JP] Japan .................................. 61-9648
Dec. 1, 1986 [JP] Japan ............................... 61-286523

[51] Int. Cl.⁴ .................... C07C 63/68; C07C 103/75
[52] U.S. Cl. ................ 562/493; 260/544 D; 564/183
[58] Field of Search ............ 260/544 D; 562/493; 564/183

[56] References Cited

U.S. PATENT DOCUMENTS 3,290,353 12/1966 Battershell et al. ............ 564/183 X
4,470,930 9/1984 Tang et al. ................ 260/544 D X
4,582,948 4/1986 Tang et al. ............... 260/544 D X

FOREIGN PATENT DOCUMENTS 0195316 9/1986 European Pat. Off. .
0207497 1/1987 European Pat. Off. .
0729186 4/1980 U.S.S.R. ........................ 260/544 D Primary Examiner—Michael L. Shippen
Attorney, Agent, or Firm—Oblon, Fisher, Spivak, McClelland & Maier

[57] ABSTRACT

The present invention is concerned with certain novel halogenobenzoic acid derivatives of the following formula, wherein R is a chlorine atom, amino group or hydroxy group, X is a chlorine atom or bromine atom, which are useful intermediates for the synthesis of antibacterial agent.

1 Claim, No Drawings

HALOGENOBENZOIC ACID DERIVATIVES AND THEIR PREPARATION

DETAILED DESCRIPTION OF THE INVENTION

The present invention is concerned with certain novel halogenobenzoic acid derivatives of the following formula,

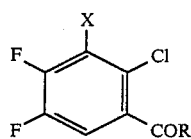

wherein R is a chlorine atom, amino group or hydroxy group, which are useful intermediates for the synthesis of medicinal compounds, especially antibacterial agents, and with a process for their preparation.

We have found that the introduction of a chlorine atom or bromine atom at the 8-position in the antibacterial quinolonecarboxylic acid analogue gives rise to enhanced activity.

Thus, 8-chloro- or 8-bromo-1-cyclopropyl-6-fluoro-1,4-dihydro-7-substituted amino-4-oxo-3-quinolinecarboxylic acid derivatives were found to be useful antibacterial agents.

The compounds of the formula (I) are synthesized as below scheme, wherein X is a chlorine atom or bromine atom.

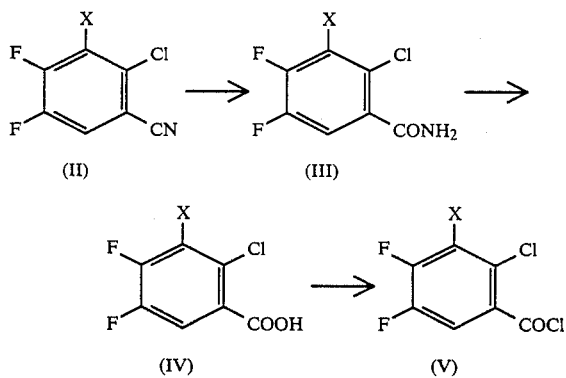

3-Chloro- or 3-bromo-2-chloro-4,5-difluorobenzonitrile (II) is hydrolyzed to 3-chloro- or 3-bromo-2-chloro-4,5-difluorobenzoic acid (IV) in the presence of an acidic catalyst or basic catalyst in a solvent such as water, methanol, ethanol, acetic acid and their mixture. Sulfuric acid, hydrochloric acid or hydrobromic acid and the like are available as the acidic catalyst. Sodium hydroxide, potassium hydroxide, calcium hydroxide and the like are available as the basic catalyst.

The reaction is preferably carried out by heating the nitrile (II) at 90° to 100° C. in sulfuric acid (2 to 50-fold volume of (IV)) and then in diluted sulfuric acid. The reaction of the nitrile with sulfuric acid affords the amide (III). The amide (III) purified or impurified, can be used for next procedure in which a mixture of (III) and diluted sulfuric acid such as 18N sulfuric acid was refluxed for several hours to give the benzoic acid (IV).

3-Chloro- or 3-bromo-2-chloro-4,5-difluorobenzoic acid (IV) is changed to 3-chloro- or 3-bromo-2-chloro-4,5-difluorobenzoyl chloride (V) on treating with a chlorination reagent such as thionyl chloride, phosphoryl chloride, phosphorous chloride and the like. It is preferable to use a catalytic amount of dimethylformamide for carrying out this reaction.

The starting compound (II) is also new and obtained, for example, from 3,4-difluoroaniline via several steps as illustrated in the following chart and in example,

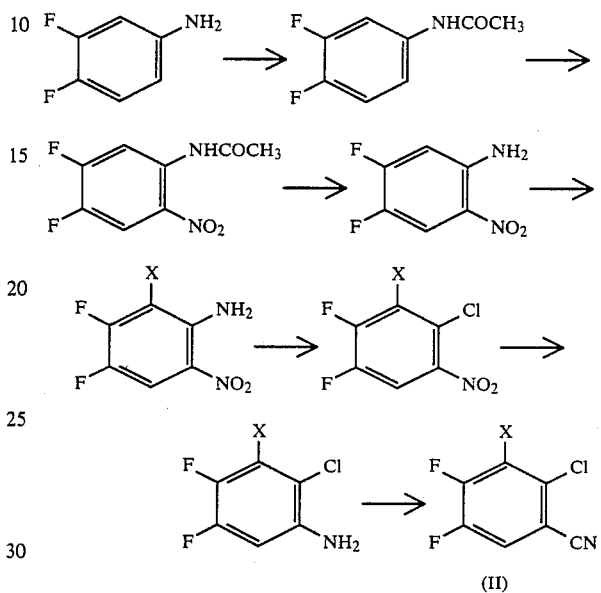

wherein X is a chlorine atom or bromine atom.

The following examples will further illustrate the invention without, however, limiting thereto.

EXAMPLE 1

2,3-Dichloro-4,5-difluorobenzamide

A solution of 2,3-dichloro-4,5-difluorobenzonitrile (1.0 g) in concentrated sulfuric acid (2.5 ml) was stirred at 90° to 100° C. for 30 minutes and then cooled. The residue was poured into ice water and the resulting precipitate was collected by filtration and recrystallized from benzene to give the title compound (0.51 g) as colorless needles, mp 153°–155° C.

Analysis (%) for $C_7H_3Cl_2F_2NO$, Calcd. (Found): C, 37.20 (37.24); H, 1.34 (1.33); N, 6.20 (6.15).

EXAMPLE 2

2,3-Dichloro-4,5-difluorobenzoic acid

A mixture of 2,3-dichloro-4,5-difluorobenzamide (0.5 g) and 18N-sulfuric acid (2.5 ml) was stirred at 125° to 135° C. for 9 hours, and then poured into ice water. After standing overnight, the resulting precipitate was collected by filtration and recrystallized from hexane-benzene to give the title compound (0.3 g) as colorless prisms.

Analysis (%) for $C_7H_2Cl_2F_2O_2$, Calcd. (Found): C, 37.04 (37.23); H, 0.89 (0.93).

EXAMPLE 3

2,3-Dichloro-4,5-difluorobenzoyl chloride

A solution of 2,3-dichloro-4,5-difluorobenzoic acid (9.3 g) and dimethylformamide (0.013 ml) in thionyl chloride (40 ml) was refluxed for 2.5 hours, and then concentrated. The resulting residue was purified by distillation in nitrogen atmosphere to give the title compound (8.7 g) as pale yellow oil, bp 123°–126° C./40 mmHg.

NMR (δ in CDCl$_3$), 7.89 (dd, J=7.5, 9.7 Hz)

Example 4

3-Bromo-2-chloro-4,5-difluorobenzoic acid

A solution of 3-bromo-2-chloro-4,5-difluorobenzonitrile (9.8 g) in concentrated sulfuric acid (10 ml) was stirred at 100° C. for 35 minutes. After cooling, 18N sulfuric acid (50 ml) and water (10 ml) were added to the reaction mixture. The reaction mixture was stirred at 100° C. for 4 hours and then poured into ice water (300 ml). The resulting precipitate was collected by filtration, washed with water sufficiently and recrystallized from dichloromethane-n-hexane to give the title compound (9.24 g) as colorless prisms, mp 137.5°–139.5° C.

Analysis (%) for C$_7$H$_2$BrClF$_2$O$_2$, Calcd. (Found): C, 30.97 (30.96); H, 0.74 (0.71).

EXAMPLE 5

3-Bromo-2-chloro-4,5-difluorobenzoyl chloride

A solution of 3-bromo-2-chloro-4,5-difluorobenzoic acid (9.0 g) in thionyl chloride (33 ml) was refluxed for 2.5 hours, and then concentrated. The resulting residue was purified by distillation to give the title compound (8.8 g), bp 109° C./22 mmHg.

NMR (δ in CDCl$_3$), 7.93 (d, J=7.5, 9.7 Hz)

In example 1 and 4, starting materials are synthesized by following process.

REFERENCE EXAMPLE 1

N-(3,4-difluorophenyl)acetamide

To 3,4-difluoroaniline (28.2 g) was added acetic anhydride (30 ml) slowly. After allowed to stand for 30 minutes, the reaction mixture was poured into ice water (100 ml). The resulting precipitate was collected by filtration and washed with water sufficiently to give the title compound (34.7 g) as colorless needles, mp 127°–127.5° C.

Analysis (%) for C$_8$H$_7$F$_2$NO, Calcd. (Found): C, 56.14 (56.15); H, 4.12 (4.06); N, 8.18 (8.00).

REFERENCE EXAMPLE 2

4,5-Difluoro-2-nitroaniline

To a solution of N-(3,4-difluorophenyl)acetamide (48 g) in concentrated sulfuric acid (140 ml) was added dropwise concentrated nitric acid (d 1.42, 56 ml) at −1° to 3° C. during 50 minutes with stirring in an ice-salt bath. After stirring for 1.5 hours at 3° to 16° C., the reaction mixture was poured into ice water (560 ml). The resulting precipitate was collected by filtration, washed with chilled water sufficiently to give N-(4,5-difluoro-2-nitrophenyl)acetamide (55.3 g).

A solution of N-(4,5-difluoro-2-nitrophenyl)acetamide (70 g) in concentrated hydrochloric acid (110 ml) and ethanol (440 ml) was refluxed for 2 hours. The reaction mixture was poured into ice water (1.5 liter) and the resulting precipitate was collected by filtration and washed with chilled water sufficiently to give the title compound (53.2 g) as yellow prisms, mp 109°–109.5° C.

Analysis (%) for C$_6$H$_4$F$_2$N$_2$O$_2$, Calcd. (Found): C, 41.39 (41.29); H, 2.32 (2.31); N, 16.09 (15.96).

REFERENCE EXAMPLE 3

2-Chloro-3,4-difluoro-6-nitroaniline

Into a solution of 4,5-difluoro-2-nitroaniline (20 g) in acetic acid (200 ml) was boubled chlorine gas at 13° to 15° C. during 45 minutes. The reaction mixture was poured into ice water (500 ml) and extracted with dichloromethane. The organic layer was washed with 6% aqueous sodium carbonate and with water successively, dried over anhydrous sodium sulfate and then concentrated. The residue was purified with silica gel chromatography eluting with dichloromethane-n-hexane (1:4) and further recrystallized from hexane to give the title compound (2.91 g) as yellow needles, mp 86°–88° C.

Analysis (%) for C$_6$H$_3$ClF$_2$N$_2$O$_2$, Calcd (Found): C, 34.56 (34.58); H, 1.45 (1.37); N, 13.43 (13.41).

REFERENCE EXAMPLE 4

2,3-Dichloro-4,5-difluoronitrobenzene

To a mixture of anhydrous cupric chloride (2.2 g) and 2-chloro-3,4-difluoro-6-nitroaniline (2.63 g) in anhydrous acetonitrile (20 ml) was added t-butylnitrite (2.0 g) dropwise at 46° to 55° C. during 9 minutes. After stirring for 13 minutes at the same temperature, the reaction mixture was poured into chilled 10% diluted hydrochloric acid (20 ml) and extracted with benzene. The organic layer was washed with diluted hydrochloric acid and with water successively, dried over anhydrous sodium sulfate and concentrated. The resulting residue was purified by silica gel chromatography eluting with dichloromethane-n-hexane (1:5) to give the title compound (2.47 g), as yellow oil.

NMR (δ in CDCl$_3$), 7.75 (dd, J=7.0, 8.8 Hz)

REFERENCE EXAMPLE 5

2,3-Dichloro-4,5-difluoroaniline

To a suspension of iron powder (1.9 g) in water (3 ml), with vigorous stirring at 50° to 60° C., was added concentrated hydrochloric acid (0.4 ml) slowly. After mixed with ethanol (7 ml), 2,3-dichloro-4,5-difluoronitrobenzene (2.47 g) in ethanol (3 ml) was added dropwise to the suspension at 54° to 66° C. during 20 minutes. After stirring for 4 hours at the same temperature, the hot reaction mixture mixed with benzene was filtered and the insoluble materials were washed with hot ethanol (5 ml) and with benzene (20 ml) successively. The filtrate and washings were combined and mixed with ice water. The resulting organic layer was collected, washed with water, dried over anhydrous sodium sulfate and then concentrated. The resulting residue was purified by silica gel chromatography eluting with dichloromethane-n-hexane (1:3) to give the title compound (0.89 g) as colorless needles, mp 94°–97.5° C.

NMR (δ in CDCl$_3$), 6.52 (dd, J=7.0, 11.4 Hz)

REFERENCE EXAMPLE 6

2,3-Dichloro-4,5-difluorobenzenediazonium tetrafluoroborate

To a suspension of 2,3-dichloro-4,5-difluoroaniline (0.88 g) in 42% fluoroboric acid (10 ml) with stirring vigorously was added sodium nitrite (0.43 g) in water (1 ml) at −15° to 0° C. for 14 minutes. After stirred for 3 hours at the same temperature, the resulting precipitate was collected by filtration, washed with 42% fluoroboric acid and then with ether to give the title compound (0.66 g) as white powdery crystals, mp 211° C.-(decompd.).

IR (KBr, cm$^{-1}$), 2300 (CN)

REFERENCE EXAMPLE 7

2,3-Dichloro-4,5-difluorobenzonitrile 2,3-Dichloro-4,5-difluorobenzenediazonium tetrafluoroborate (0.65 g) was added portionwise during 10 minutes to a solution of cuprous cyanide (0.4 g), potassium cyanide (0.58 g) and sodium carbonate (0.12 g) in water (10 ml) with stirring vigorously at room temperature. After the mixture was stirred for 2.8 hours, benzene (20 ml) was added to the suspension and then the mixture was stirred for 15 minutes. The insoluble materials were collected by filtration, and washed with benzene. The filtrate and washings were combined and washed with water, dried over anhydrous sodium sulfate and then concentrated. The resulting residue was purified by silica gel chromatography eluting with dichloromethane-n-hexane (1:3) to give the title compound (0.15 g), mp 46.5°–49.5° C.

NMR (δ in CDCl$_3$), 7.49 (dd, J=7.3, 8.6 Hz)
IR (KBr, cm$^{-1}$), 2260 (CN)
Mass m/e; 207 (M+), 209 (M++2), 211 (M++4),
Calcd. MW. 207.99 for C$_7$HCl$_2$F$_2$N

REFERENCE EXAMPLE 8

2-Bromo-3,4-difluoro-6-nitroaniline

Into a solution of 4,5-difluoro-2-nitroaniline (3.7 g) in acetic acid (27 ml) was added bromine (6.8 g) dropwise at 50° to 56° C. and stirred for 2.5 hours. The reaction mixture was poured into ice water (60 ml) and the resulting precipitate was collected by filtration and washed with water sufficiently to give the title compound (4.7 g) as yellow prisms, mp 105° C.

Analysis (%) for C$_6$H$_3$BrF$_2$N$_2$O$_2$, Calcd. (Found): C, 28.48 (28.62); H, 1.20 (1.15); N, 11.07 (11.00).

REFERENCE EXAMPLE 9

3-Bromo-2-chloro-4,5-difluoronitrobenzene

To a mixture of anhydrous cupric chloride (3.1 g) and 2-bromo-3,4-difluoro-6-nitroaniline (4.6 g) in anhydrous acetonitrile (30 ml) was added t-butylnitrite (2.8 g) dropwise at 51° to 56° C. during 5 minutes. After stirring for 8 minutes at the same temperature, the reaction mixture was poured into chilled 10% diluted hydrochloric acid (30 ml) and extracted with benzene. The organic layer was washed with diluted hydrochloric acid and with water successively, dried over anhydrous sodium sulfate and concentrated. The resulting residue was purified by silica gel chromatography eluting with dichloromethane-n-hexane (1:5) to give the title compound (4.0 g).

NMR (δ in CDCl$_3$), 7.79 (d, J=7.0, 8.8 Hz)

REFERENCE EXAMPLE 10

3-Bromo-2-chloro-4,5-difluoroaniline

To a suspension of iron powder (38.6 g) in water (40 ml), with stirring vigorously at 50° to 60° C., was slowly added concentrated hydrochloric acid (5 ml). After mixed with ethanol (100 ml), 3-bromo-2-chloro-4,5-difluoronitrobenzene (58.8 g) was added portionwise to the suspension at 60° to 75° C. during 30 minutes. After stirring for 70 minutes, the hot reaction mixture was filtered and the insoluble materials were washed with hot ethanol (30 ml) and with benzene (100 ml) successively. The filtrate and washings were combined and mixed with ice water. The resulting organic layer was washed with water, dried over anhydrous sodium sulfate and then concentrated. The resulting residue was purified by silica gel chromatography eluting with dichloromethane-n-hexane (1:1) to give the title compound (34.5 g) as light brown prisms, mp 83°–86° C.

REFERENCE EXAMPLE 11

3-Bromo-2-chloro-4,5-difluorobenzenediazonium tetrafluoroborate

To a suspension of 3-bromo-2-chloro-4,5-difluoroaniline (30.1 g) in 42% fluoroboric acid (180 ml) with stirring vigorously was added sodium nitrite (12 g) in water (30 ml) at −9° to 1° C. for 40 minutes. After stirred for 1.5 hours, the resulting precipitate was collected by filtration and washed with 42% fluoroboric acid and then with ether to give the title compound (35.6 g) as light yellow needles, mp>300° C.

IR (KBr, cm$^{-1}$); 2280 (—N≡N+)

REFERENCE EXAMPLE 12

3-Bromo-2-chloro-4,5-difluorobenzonitrile

3-Bromo-2-chloro-4,5-difluorobenzenediazonium tetrafluoroborate (35.6 g) was added portionwise during 40 minutes to a solution of cuprous cyanide (18.67 g), potassium cyanide (27.14 g) and sodium carbonate (5.52 g) in water (200 ml) with stirring vigorously at room temperature. After the mixture was stirred for 4.5 hours, benzene (250 ml) was added to the suspension and then the mixture was stirred for 25 minutes. The insoluble materials were collected by filtration, and washed with benzene. The filtrate and washings were combined and washed with water, dried over ahhydrous sodium sulfate and then concentrated. The resulting residue was purified by silica gel chromatography eluting with dichloromethane-n-hexane (1:3) and further recrystallized from n-hexane-dichloromethane to give the title compound (10.9 g) as light yellow needles, mp 71°–72.5° C.

Analysis (%) for C$_7$HBrClF$_2$N, Calcd. (Found): C, 33.31 (33.22); H, 0.40 (0.31); N, 5.55 (5.48).

What is claimed is:

1. A compound of the formula (I);

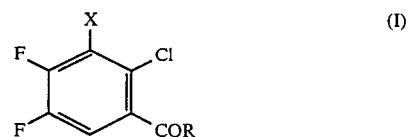

wherein R is a chlorine atom, amino group or hydroxy group, X is a chlorine or bromine atom.

* * * * *